United States Patent [19]

Breton et al.

[11] Patent Number: 5,900,242
[45] Date of Patent: May 4, 1999

[54] COSMETIC/DERMATOLOGICAL SKIN CARE COMPOSITIONS COMPRISING S-DHEA

[75] Inventors: Lionel Breton, Versailles; Olivier de Lacharriere, Paris, both of France

[73] Assignee: Société L'Oréal S.A., Paris, France

[21] Appl. No.: 08/899,880

[22] Filed: Jul. 24, 1997

Related U.S. Application Data

[62] Division of application No. 08/592,175, Jan. 26, 1996.

[30] Foreign Application Priority Data

Jan. 26, 1995 [FR] France .................. 95 00899

[51] Int. Cl.$^6$ ........................ A61K 9/48
[52] U.S. Cl. .......... 424/401; 424/450; 424/489; 514/844; 514/937; 514/944
[58] Field of Search .................. 424/401, 450, 424/489; 514/844, 937, 944

[56] References Cited

U.S. PATENT DOCUMENTS 4,496,556  1/1985  Orentreich ................ 514/178
4,542,129  9/1985  Orentreich ................ 514/178

FOREIGN PATENT DOCUMENTS 0189738  8/1986  European Pat. Off. .
2405068  5/1979  France .
9416709  8/1994  WIPO .

OTHER PUBLICATIONS

Chemical Abstracts, vol. 104, No. 2, Jan. 13, 1986, Columbus, Ohio, USA; Abstract No. 10399s, p. 302, col. G; & JP–A–60 161 912 (Kanebo, Ltd).

Primary Examiner—Jyothsna Venkat
Attorney, Agent, or Firm—Burns, Doane, Swecker & Mathis, L.L.P.

[57] ABSTRACT

Dehydro-epi-androsterone sulfate, topically applied, is well suited for therapeutically treating human skin wrinkles and fine lines and/or for combating cutaneous and/or subcutaneous slackening and/or for reviving the radiance of the skin.

9 Claims, No Drawings

COSMETIC/DERMATOLOGICAL SKIN CARE COMPOSITIONS COMPRISING S-DHEA

This application is a divisional, of application Ser. No. 08/592,175, filed Jan. 26 1996.

BACKGROUND OF THE INVENTION

1. Technical Field of the Invention

The present invention relates to novel cosmetic/dermatological compositions for topical application to human skin, comprising sodium dehydroisoandrosterone 3-sulfate, also termed dehydro-epi-androsterone sulfate, or known by the simple abbreviation "S-DHEA," and to the use of same for treating certain signs of endogenous and/or exogenous aging.

2. Description of the Prior Art

Cutaneous aging results from the effects on the skin of intrinsic and extrinsic factors. Clinically, the signs of aging are reflected by the appearance of wrinkles and fine lines, by a slackening of cutaneous and subcutaneous tissue, by a loss of cutaneous elasticity, by atonia of the texture of the skin and by the yellowing of the skin which becomes duller and loses its radiance. On the areas of the skin which have been exposed to sunlight throughout life - essentially the face, the neckline, the hands and the forearms - pigmentation marks, telangiectasia and elastosis are often observed.

Certain of these signs are more particularly associated with intrinsic or physiological aging, namely, aging associated with age, whereas others are more specific to extrinsic aging, namely, aging caused by the environment in general; this relates more particularly to photoaging due to exposure to sunlight, to light or to any other radiation.

The changes in the skin resulting from intrinsic or physiological aging are the consequence of a genetically programmed senescence involving endogenous factors. This intrinsic aging causes, in particular, a slowing down in the rate of regeneration of skin cells. Histologically, the skin is overall rendered thinner, both at the epidermal and dermal levels. The density of the fibrous macromolecules of the dermis (elastin and collagen) is reduced. In contrast, extrinsic aging effects histopathological changes such as excessive accumulation of elastic matter in the upper dermis and degeneration of the collagen fibers.

In general, skin aging manifests itself in the appearance of wrinkles and fine lines, with the slackening of cutaneous and subcutaneous tissue and with the radiance of the skin. Slackening of the cutaneous and subcutaneous tissue is reflected in a skin texture lacking tone, slackening of the cutaneous microrelief, reduced skin firmness and an overall flaccid skin.

Numerous compositions are known to this art for treating wrinkles and fine lines on the skin or to firm skin tissue; however, these compositions provide only incomplete and temporary treatment of these morphological disorders. Thus, serious need continues to exist for a topical-application composition which makes it possible to treat wrinkles and fine lines more effectively, as well as to firm skin tissue.

SUMMARY OF THE INVENTION

Accordingly, a major object of the present invention is the provision of improved skin care compositions for treating wrinkles and fine lines, and for firming skin tissue.

Another object of this invention is the provision of improved skin care compositions for imparting to old skin a radiance comparable to that of a younger skin.

Briefly, the present invention features novel cosmetic/dermatological skin care topical compositions for treating wrinkles and fine lines and/or for combating cutaneous and/or subcutaneous slackening and/or for reviving the radiance of the skin, and which comprise a therapeutically effective amount of dehydro-epi-androsterone sulfate.

This invention also features the cosmetic/dermatological treatment of wrinkles and/or fine lines and/or of cutaneous and/or subcutaneous slackening and/or sagging (or collapse) for the purpose of firming the skin and/or for reviving the radiance of the skin, and/or for toning up the texture thereof, comprising topically applying thereto a cosmetic/dermatological composition containing a therapeutically effective amount of dehydro-epi-androsterone sulfate.

DETAILED DESCRIPTION OF BEST MODE AND SPECIFIC/PREFERRED EMBODIMENTS OF THE INVENTION

More particularly according to the present invention, The subject compositions contain a cosmetically or dermatologically acceptable medium (vehicle, diluent or carrier), namely, one which is compatible with skin tissue. Thus, these compositions may be applied to the entire human body.

The S-DHEA is employed, for example, in an amount advantageously ranging from 0.00001% to 5% of the total weight of the composition, preferably from 0.0001% to 1% and, more preferably, from 0.001% to 0.5%.

The compositions according to the invention may comprise all pharmaceutical formulations used conventionally for topical application and, in particular, are in the form of aqueous, aqueous/alcoholic or oily solutions, dispersions of the lotion or serum type, anhydrous or lipophilic gels, emulsions of liquid or semi-liquid consistency of the milk type, which are obtained by dispersion of a fatty phase in an aqueous phase (O/W) or conversely (W/o), or suspensions or emulsions of smooth, semi-solid or solid consistency of the cream or gel type, or alternatively microemulsions, microcapsules, microparticles or vesicle dispersions of ionic and/or nonionic type. These compositions are formulated according to the usual techniques well known to this art.

When the compositions of the invention are formulated as an emulsion, the proportion of the fatty phase may range from 5% to 80% by weight, and preferably from 5% to 50% by weight, relative to the total weight of the composition. The oils, the emulsifiers and the coemulsifiers incorporated in the composition in emulsion form are selected from among those used conventionally in the cosmetic or dermatological field. The emulsifer and coemulsifier are advantageously present in the composition at a proportion ranging from 0.3% to 30% by weight, and preferably from 0.5% to 20% by weight, relative to the total weight of the composition. The emulsion may also contain lipid vesicles.

When the compositions of the invention are formulated as an oily solution or gel, the fatty phase may constitute more than 90% of the total weight of the composition.

In known manner, the cosmetic or dermatological compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, sunscreens, bactericides, odor absorbers and dyestuffs or colorants. The amounts of these various additives and adjuvants are those conventionally used in the particular field, and, for example, range from 0.01% to 10% of the total weight of the composition. Depending on their nature, these additives and adjuvants may be introduced into the fatty phase, into the aqueous phase and/or into the lipid spherules.

Exemplary oils which may be used according to this invention include mineral oils (liquid petrolatum), plant oils (liquid fraction of karite butter, sunflower oil), animal oils (perhydrosqualene), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Exemplary emulsifiers which may be used include glyceryl stearate, polysorbate 60 and the PEG-6/PEG-32/glycol stearate mixture marketed under the trademark Tefose® 63 by Gattefosse.

Exemplary solvents which may be used include the lower alcohols, in particular ethanol and isopropanol, and propylene glycol.

Exemplary hydrophilic gelling agents according to this invention include carboxyvinyl polymers (carbomer), acrylic copolymers such as acrylate/alkylacrylate copolymers, polyacrylamides, polysaccharides such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

And exemplary lipophilic or hydrophilic active agents which may be used for the purpose of improving the treatment of wrinkles and fine lines, improving combating cutaneous and/or subcutaneous slackening and/or improving the radiance of the skin, include, for example, retinoids (retinol and esters thereof, retinal, retinoic acid and derivatives thereof, retinoids, in particular those described in FR-A-2,570,377, EP-A-199,636, EP-A-325,540 and EP-A-402,072), α-hydroxy acids (glycolic acid, lactic acid, malic acid, citric acid, tartaric acid and mandelic acid), β-hydroxy acids (salicylic acid and derivatives thereof, in particular alkylated derivatives), α-keto acids, β-keto acids, peroxides such as benzoyl peroxide, vitamins, in particular vitamins E and F, anti-free radical agents such as superoxide dismutase, selenium, zinc and beta-carotenes.

The subject compositions may also contain hormones other than S-DHEA, which may be natural or synthetic and estrogenic, progestative or androgenic, such as progesterone, testosterone, anhydrous estradiol, broparoestrol, estrone, pregnenolone acetate, pregnenolone, 17-beta-hydroxyprogesterone, testosterone propionate, adrostenedione and androstanediols.

In order to further illustrate the present invention and the advantages thereof, the following specific examples are given, it being understood that same are intended only as illustrative and in nowise limitative.

In said examples to follow, all parts and percentages are given by weight.

EXAMPLE 1:
Cream for combating the slackening of skin tissue (oil-in-water emulsion):

| | |
|---|---|
| Na S-DHEA | 0.05 |
| Glyceryl stearate | 2.00 |
| Polysorbate 60 (Tween 60 marketed by ICI) | 1.00 |
| Stearic acid | 1.40 |
| Triethanolamine | 0.70 |
| Carbomer | 0.40 |
| Corn germ oil | 12.00 |
| Sunflower oil | 10.00 |
| Antioxidant | 0.05 |
| Fragrance | 0.50 |
| Preservative | 0.30 |
| Water | qs 100% |

EXAMPLE 2:
Facial anti-wrinkle care cream (oil-in-water emulsion):

| | |
|---|---|
| Na S-DHEA | 0.10 |
| Glyceryl stearate | 2.00 |
| Polysorbate 60 (Tween 60 marketed by ICI) | 1.00 |
| Stearic acid | 1.40 |
| 5-n-Octanoylsalicylic acid | 0.50 |
| Triethanolamine | 0.70 |
| Carbomer | 0.40 |
| Sunflower oil | 12.00 |
| Silicone oil | 12.00 |
| Antioxidant | 0.05 |
| Fragrance | 0.50 |
| Preservative | 0.30 |
| Water | qs 100% |

EXAMPLE 3:
Cream for restoring the radiance to old skin:

| | |
|---|---|
| Na S-DHEA | 0.03 |
| Estrone | 0.005 |
| Estradiol | 0.005 |
| Pregnenolone acetate | 0.01 |
| Hydrogenated castor oil | 12.00 |
| Sunflower oil | 8.00 |
| Polysorbate 60 | 1.00 |
| Glyceryl stearate | 2.00 |
| Carbomer | 0.40 |
| Triethanolamine | 0.70 |
| Antioxidant | 0.05 |
| Fragrance | 0.05 |
| Preservative | 0.30 |
| Water | qs 100% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for reviving the radiance of human skin, comprising topically applying a composition comprising a therapeutically effective amount of dehydro-epi-androsterone sulfate ("S-DHEA") in a cosmetically or dermatologically acceptable vehicle, carrier or diluent therefor.

2. The method of claim 1, which further comprises topically applying an active agent selected from the group consisting of a hydrophilic agent, lipophilic gelling agent, hydrophilic bioactive agent, lipophilic bioactive agent, preservative, antioxidant, solvent, fragrance, filler, sunscreen, bactericide, odor absorber, dyestuff, colorant, and combinations thereof.

3. The method according to claim 1 which further comprises topically applying an active agent selected from the group consisting of a retinoid, α-hydroxy acid, β-hydroxy acid, α-keto acid, β-keto acid, benzoyl peroxide, vitamin, anti-free radical agent, and combinations thereof.

4. The method according to claim 1, which further comprises topically applying an additional active agent selected from the group consisting of an estrogenic hormone, progestative hormone, and an androgenic hormone other than S-DHEA.

5. The method according to claim 4 further comprising topically applying at least one hormone other than S-DHEA which is selected from the group consisting of progesterone, testosterone, anhydrous estradiol, broparoestrol, estrone, pregnenolone acetate, pregnenolone, 17-beta-hydroxyprogesterone, testosterone, propionate, adrostenedione, an androstanediol, and combinations thereof.

6. The method according to claim 1, wherein the topically applied composition comprises from 0.00001% to 5% by weight of S-DHEA.

7. The method according to claim 6, wherein the topically applied composition comprises from 0.0001% to 1% by weight of S-DHEA.

8. The method according to claim 7, wherein the topically applied composition comprises from 0.001% to 0.5% by weight of S-DHEA.

9. The method according to claim 1, wherein the topically applied composition is selected from the group consisting of an aqueous, aqueous/alcoholic and oily solution dispersion, a gel, emulsion, a cream, a lotion, a microemulsion, microcapsule containing composition, microparticle containing composition, and a vesicle dispersion.

* * * * *